US011534099B2

United States Patent
Ma et al.

(10) Patent No.: US 11,534,099 B2
(45) Date of Patent: Dec. 27, 2022

(54) SYSTEMS AND METHODS FOR DETERMINING AN ARRHYTHMIA TYPE

(71) Applicant: VITA-COURSE TECHNOLOGIES CO., LTD., Guangdong (CN)

(72) Inventors: Ruiqing Ma, Shenzhen (CN); Chuanmin Wei, Shenzhen (CN); Jiwei Zhao, Shenzhen (CN); Zhiyong Wang, Shenzhen (CN)

(73) Assignee: VITA-COURSE TECHNOLOGIES CO., LTD., Shenzhen (CN)

( * ) Notice: Subject to any disclaimer, the term of this patent is extended or adjusted under 35 U.S.C. 154(b) by 122 days.

(21) Appl. No.: 17/044,262

(22) PCT Filed: Apr. 27, 2018

(86) PCT No.: PCT/CN2018/084728
§ 371 (c)(1),
(2) Date: Sep. 30, 2020

(87) PCT Pub. No.: WO2019/205067
PCT Pub. Date: Oct. 31, 2019

(65) Prior Publication Data
US 2021/0022633 A1 Jan. 28, 2021

(51) Int. Cl.
*A61B 5/00* (2006.01)
*A61B 5/341* (2021.01)
(Continued)

(52) U.S. Cl.
CPC ........... *A61B 5/341* (2021.01); *A61B 5/0006* (2013.01); *A61B 5/361* (2021.01); *A61B 5/363* (2021.01);
(Continued)

(58) Field of Classification Search
CPC ............ A61B 5/346–366; A61B 5/7235–7267
See application file for complete search history.

(56) References Cited

U.S. PATENT DOCUMENTS 5,819,007 A * 10/1998 Elghazzawi ......... A61B 5/7264
706/924
2008/0221633 A1 9/2008 Linker

FOREIGN PATENT DOCUMENTS

| CN | 104398252 A | 3/2015 |
| CN | 105748063 A | 7/2016 |
| CN | 107657318 A | 2/2018 |

OTHER PUBLICATIONS

Li Li et al., Study on Prevention and Treatment of Sudden Cardiac Death Caused by Heart Failure, Journal of China Traditional Chinese Medicine Information, 2010, 2 pages.
(Continued)

*Primary Examiner* — Scott M. Getzow
(74) *Attorney, Agent, or Firm* — Metis IP LLC

(57) ABSTRACT

Systems and methods for determining an arrhythmia type are provided. A method may include: obtaining an electrocardiogram signal, obtaining a feature vector of the electrocardiogram signal, obtaining a trained prediction model, and determining an arrhythmia type of the electrocardiogram signal based on the trained prediction model and the feature vector. The feature vector includes a threshold crossing sample (TCSC) percent feature, an L-Z complexity feature, an empirical mode decomposition (EMD) complex number feature, a sample entropy feature, and a set of wavelet transform energy features.

17 Claims, 8 Drawing Sheets

(51) Int. Cl.
G06N 20/10 (2019.01)
A61B 5/361 (2021.01)
A61B 5/363 (2021.01)

(52) U.S. Cl.
CPC ............ *A61B 5/7264* (2013.01); *A61B 5/746* (2013.01); *G06N 20/10* (2019.01)

(56) References Cited

OTHER PUBLICATIONS

Zhi-Jie Zheng et al., Sudden Cardiac Death in the United States, 1989 to 1998, Circulation, 104(18):2158-2163, 2091.

Dayi Hu, Prevention of Risk Factors of Sudden Cardiac Death, Chinese Journal of Cardiac Pacing and Electrophysiology, 20(5), 2006, 3 pages.

Eleftheria P. Tsagalou et al., Time Course of Fibrillation and Defibrillation Thresholds After an Intravenous Bolus of Amiodarone—an Experimental Study, Resuscitation, 61: 83-89, 2004.

Muhammad Abdullah Arafat et al., A Simple Time Domain Algorithm for the Detection of Ventricular Fibrillation in Electrocardiogram, Computers in Biology and Medicine, (5): 1-10, 2011.

Abraham Lempel et al., On the Complexity of Finite Sequences, IEEE Transactions on Information Theory, 22(1):75-81, 1976.

Norden E. Huang et al., The Empirical Mode Decomposition and the Hilbert Spectrum for Nonlinear and Non-stationary Time Series Analysis, Proceedings of the Royal Society of London, 454: 903-995, 1998.

Don Lerro et al., Tracking with Debiased Consistent Converted Measurements Verus EKF, IEEE Transactions on Aerospace and Electronic Systems, 29(3): 1015-1022, 1993.

G.Selvakumar et al., Wavelet Decomposition for Detection and Classification of Critical ECG Arrhythmias, Proceedings of the 8th WSEAS Int. Conference on Mathematics and Computers in Biology and Chemistry, 2007, 5 pages.

Nitish V. Thakor et al., Estimation of QRS Complex Power Spectra for Design of a QRS Filter, IEEE Transactions on Biomedical Engineering, 31(11): 702-706, 1984.

A. S. Al-Fahoum et al., Combined Wavelet Transformation and Radial Basis Neural Networks for Classifying Life-threatening Cardiac Arrhythmias, Medical & Biological Engineering & Computing, 37: 566-573, 1999.

Ruiqing MA, Ventricular Fibrillation Detection Algorithms Based on Time-Frequency Domain, Harbin Institute of Technology, 2012, 57 pages.

International Search Report in PCT/CN2018/084728 dated Feb. 1, 2019, 5 pages.

Written Opinion in PCT/CN2018/084728 dated Feb. 1, 2019, 4 pages.

\* cited by examiner

SYSTEMS AND METHODS FOR DETERMINING AN ARRHYTHMIA TYPE

CROSS-REFERENCE TO RELATED APPLICATIONS

This application is a U.S. national stage under 35 U.S.C. § 371 of International Application No. PCT/CN2018/084728, filed on Apr. 27, 2018, the contents of which are hereby incorporated herein by reference.

TECHNICAL FIELD

The present disclosure generally relates to medical devices, and in particular, to systems and methods for determining an arrhythmia type of an electrocardiogram.

BACKGROUND

Ventricular Fibrillation (VF), Ventricular Tachycardia (VT), Ventricular Flutter (VFL), and Supraventricular tachycardia (SVT) are four types of arrhythmia. VF is a heart rhythm problem due to disorganized electrical activity in the ventricles. The ventricular muscle twitches randomly, so the ventricles fail to pump blood around the body. VF is one of the common causes of sudden cardiac death. VT is a heart rhythm disorder characterized by a wide malformation of the QRS complexes three or more times in succession, with a frequency exceeding 100 beats/min. VFL is a transitional heart rate between the VT and VF. VFL often lasts a short period. Most patients develop into VF in a few minutes, and some VF patients may VT. SVT is defined as an abnormally fast heartbeat. P waves of Supraventricular tachycardia (SVT) may be difficult to identify, and QRS complexes are the same as those of a patient with sinus. The frequency of SVT is 150 to 240 times per minute, and the rhythm is uniform.

In some cases, when a patient has VT, he or she should seek medical attention immediately; otherwise, it is very likely to develop into VF. The faster the detection of VF, the higher the success rate of saving the patient. The existing methods of classifying different types of arrhythmia (e.g., VT, VF, SVT, VFL) are to extract from arrhythmia electrocardiograph (ECG) signals certain characteristics, such as P wave, QRS complex, T wave, RR period (a time period between two R wave in two QRS complexes), ST segment (the period of a flat line from the end of the QRS complex to the start of T wave), etc., and classify the types of arrhythmia based on such characteristics. However, some waves of the arrhythmia electrocardiograph (ECG) become deformed, it is difficult to classify arrhythmia types. Accordingly, it is desirable to provide systems and methods for detecting and classify different types of arrhythmia quickly and accurately.

SUMMARY

According to an aspect of the present disclosure, a system configured to determine an arrhythmia type may include at least one storage device including a set of instructions for determining an arrhythmia type, and at least one processor in communication with the storage device, wherein when executing the set of instructions, the at least one processor may be directed to: obtain an electrocardiogram signal; obtain a feature vector of the electrocardiogram signal; obtain a trained prediction model, and determine an arrhythmia type of the electrocardiogram signal based on the trained prediction model and the feature vector.

In some embodiments, the feature vector may include a threshold crossing sample (TCSC) percent feature, an L-Z complexity feature, an empirical mode decomposition (EMD) complex number feature, a sample entropy feature, and a set of wavelet transform energy features.

In some embodiments, to obtain the trained prediction model, the at least one processor is further directed to: obtain training samples including a plurality of arrhythmia types of historical electrocardiogram signals; obtain feature vectors of the training samples; obtain a preliminary prediction model, the preliminary prediction model including a classifier model; and train the preliminary prediction model to obtain the trained prediction model using the training samples and the feature vectors of the training samples as inputs of the classifier model.

In some embodiments, the classifier model may include at least one of: a random forest model, a BP neural network model, a support vector machine (SVM) model, or a wavelet neural network model.

In some embodiments, to train the preliminary prediction model to obtain the trained prediction model, the at least one processor is further directed to: train the preliminary prediction model to obtain an intermediate prediction model using the training samples and the feature vectors of the training samples as the inputs of the classifier model; obtain testing samples including a plurality of arrhythmia types of historical electrocardiogram signals; obtain feature vectors of the testing samples; determine an accuracy rate of the intermediate prediction model based on the testing samples and the feature vector of the testing samples, wherein the testing samples and the feature vectors of the testing samples are inputs of the intermediate prediction model; determine whether the accuracy rate is greater than an accuracy rate threshold; and designate the intermediate prediction model based on a result of the determination that the accuracy rate is greater than the accuracy rate threshold.

In some embodiments, to train the preliminary prediction model to obtain the trained prediction model, the at least one processor is further directed to: re-train the intermediate prediction model based on a result of the determination that the accuracy rate is not greater than the accuracy rate threshold.

In some embodiments, the arrhythmia type includes at least one of: a Ventricular Fibrillation (VF), a Ventricular Tachycardia (VT), a Ventricular Flutter (VFL), or a Supraventricular tachycardia (SVT).

According to another aspect of the present disclosure, a method for determining an arrhythmia type may be implemented on a computing device having at least one processor and at least one storage device. The method may include one or more following operations: obtaining an electrocardiogram signal; obtaining a feature vector of the electrocardiogram signal; obtaining a trained prediction model; and determining an arrhythmia type of the electrocardiogram signal based on the trained prediction model and the feature vector.

In some embodiments, the feature vector includes a threshold crossing sample (TCSC) percent feature, an L-Z complexity feature, an empirical mode decomposition (EMD) complex number feature, a sample entropy feature, and a set of wavelet transform energy features.

In some embodiments, training the prediction model may include one or more following operations: obtaining training samples including a plurality of arrhythmia types of historical electrocardiogram signals; obtaining feature vectors of the training samples; obtaining a preliminary prediction model, the preliminary prediction model including a classifier model; and training the preliminary prediction model to obtain the trained prediction model using the training samples and the feature vectors of the training samples as inputs of the classifier model.

In some embodiments, the classifier model includes at least one of: a random forest model, a BP neural network model, a support vector machine (SVM) model, or a wavelet neural network model.

In some embodiments, training the preliminary prediction model to obtain the trained prediction model may include one or more following operations: training the preliminary prediction model to obtain an intermediate prediction model using the training samples and the feature vectors of the training samples as the inputs of the classifier model; obtaining testing samples including a plurality of arrhythmia types of historical electrocardiogram signals; obtaining feature vectors of the testing samples; determining an accuracy rate of the intermediate prediction model based on the testing samples and the feature vector of the testing samples, wherein the testing samples and the feature vectors of the testing samples are inputs of the intermediate prediction model; determining whether the accuracy rate is greater than an accuracy rate threshold; and designating the intermediate prediction model based on a result of the determination that the accuracy rate is greater than the accuracy rate threshold.

In some embodiments, training the preliminary prediction model to obtain the trained prediction model may include the following operation: re-training the intermediate prediction model based on a result of the determination that the accuracy rate is not greater than the accuracy rate threshold.

In some embodiments, the arrhythmia type includes at least one of: a Ventricular Fibrillation (VF), a Ventricular Tachycardia (VT), a Ventricular Flutter (VFL), or a Supraventricular tachycardia (SVT).

According to still another aspect of the present disclosure, a non-transitory computer-readable medium may include at least one set of instructions for determining an arrhythmia type, when executed by at least one processor of a computer device, the at least one set of instructions directs the at least one processor to: obtain an electrocardiogram signal; obtain a feature vector of the electrocardiogram signal; obtain a trained prediction model; and determine an arrhythmia type of the electrocardiogram signal based on the trained prediction model and the feature vector.

According to still another aspect of the present disclosure, a system configured to determine an arrhythmia type may include one or more following modules: a signal obtaining module configured to obtain an electrocardiogram signal; a feature extracting module configured to obtain a feature vector of the electrocardiogram signal; a prediction model storing module configured to obtain a trained prediction model; and an arrhythmia type determining module configured to determine an arrhythmia type of the electrocardiogram signal based on the trained prediction model and the feature vector.

BRIEF DESCRIPTION OF THE DRAWINGS

The present disclosure is further described in terms of exemplary embodiments. The foregoing and other aspects of embodiments of present disclosure are made more evident in the following detail description when read in conjunction with the attached drawing figures.

DETAILED DESCRIPTION

Figure 1:
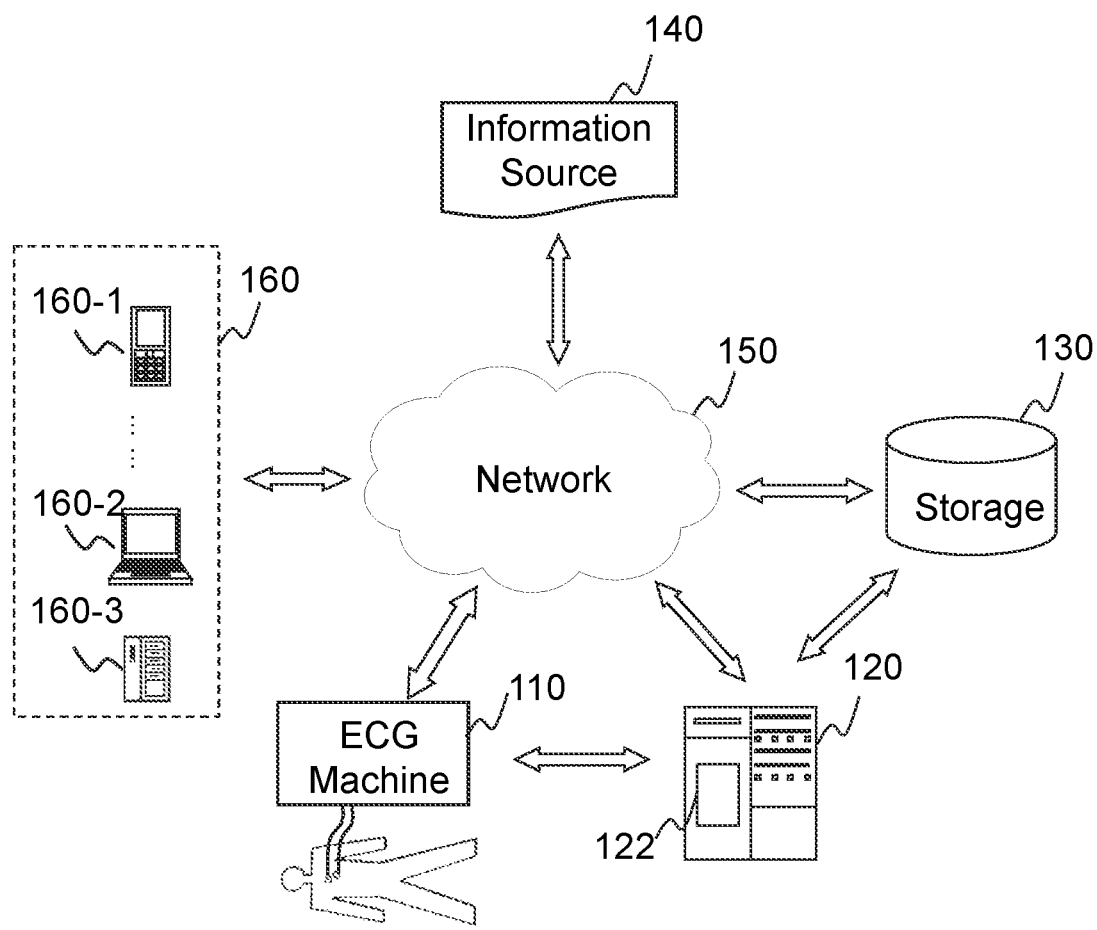
FIG. 1 is a block diagram of an exemplary system for determining an arrhythmia type of an electrocardiogram signal according to some embodiments of the present disclosure.

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order or simultaneously. Moreover, one or more other operations may be added to the flowcharts. One or more operations may be removed from the flowcharts.

Moreover, while the system and method in the present disclosure are described primarily in regard to electrocardiograph examination, it should also be understood that this is only one exemplary embodiment. The application scenarios of the system or method of the present disclosure may include a physical examination, a diagnosis, a monitor, or the like, or a combination thereof.

One aspect of the present disclosure relates to systems and methods for determining an arrhythmia type for an electrocardiogram signal. According to the present disclosure, the systems and methods may train a prediction model to predict an arrhythmia type of an electrocardiogram signal based on five features of the electrocardiogram signal. The five features may include a percent of the number of samples that are greater than a number threshold, a complexity value determined according to an L-Z Complexity Measure Algorithm, a complex number determined according to EMD method, and a set of wavelet transform energy including an energy of the fourth decomposition, an energy of the sixth decomposition, and an energy of the seventh decomposition of the electrocardiogram signal.

FIG. 1 is a block diagram of an exemplary system for determining an arrhythmia type of an electrocardiogram signal according to some embodiments of the present disclosure. For example, the system 100 may be a signal processing platform for an electrocardiogram (ECG) signal obtained from an electrocardiograph machine (ECG machine), a multi-parameter monitor, a dynamic Holter, a wearable device, a storage device storing a plurality of ECG signals, or the like, or a combination thereof. The system 100 may include an ECG machine 110, a server 120, a storage device 130, an information source 140, a network 150, and a user terminal 160.

The ECG machine 110 may be configured to obtain electrocardiogram signals from a living being. For example, the ECG machine 110 may record electrical activities of the heart over a period of time using electrodes placed on the skin of a living being (e.g., a human being, an animal). The electrodes may detect electrical changes on the skin that arise from the heart muscle's electro-physiologic pattern during each heartbeat. In some embodiments, the ECG machine 110 may also refer to ECG electrodes in a multi-parameter monitor, a dynamic Holter, a wearable device, etc., that may obtain electrocardiogram signals.

The server 120 may be configured to process information and/or data relating to the electrocardiogram signals. For example, the server 120 may determine an arrhythmia type of an electrocardiogram signal obtained from the ECG machine 110. As another example, the server 120 may process a plurality of electrocardiogram signals obtained from the ECG machine 110 and/or stored in the storage device 130 to determine a method and/or algorithm (e.g., a model) to predict an arrhythmia type of an electrocardiogram signal. In some embodiments, the server 120 may be a single server or a server group. The server group may be centralized, or distributed (e.g., the server 120 may be a distributed system). In some embodiments, the server 120 may be local or remote. For example, the server 120 may access information and/or data stored in the user terminal 160 and/or the storage device 130 via the network 150. As another example, the server 120 may be directly connected to the user terminal 160, and/or the storage device 130 to access stored information and/or data. In some embodiments, the server 120 may be implemented on a cloud platform. Merely by way of example, the cloud platform may include a private cloud, a public cloud, a hybrid cloud, a community cloud, a distributed cloud, an inter-cloud, a multi-cloud, or the like, or a combination thereof. In some embodiments, the server 120 may be implemented on a computing device having one or more components illustrated in FIG. 2 in the present disclosure.

In some embodiments, the server 120 may include a processing engine 122. The processing engine 122 may process information and/or data relating to the electrocardiogram signals to perform one or more functions described in the present disclosure. For example, the processing engine 122 may process a plurality of electrocardiogram signals obtained from the ECG machine 110 and/or stored in the storage device 130 to determine a method and/or algorithm (e.g., a model) to predict an arrhythmia type of an electrocardiogram signal. As another example, the processing engine 122 may predict an arrhythmia type of an electrocardiogram signal based on a prediction method and/or algorithm (e.g., a model). In some embodiments, the processing engine 122 may include one or more processing engines (e.g., single-core processing engine(s) or multi-core processor(s)). Merely by way of example, the processing engine 122 may include a central processing unit (CPU), an application-specific integrated circuit (ASIC), an application-specific instruction-set processor (ASIP), a graphics processing unit (GPU), a physics processing unit (PPU), a digital signal processor (DSP), a field programmable gate array (FPGA), a programmable logic device (PLD), a controller, a microcontroller unit, a reduced instruction-set computer (RISC), a microprocessor, or the like, or a combination thereof. In some embodiments, the processing engine 122 may include a logic circuit. The logic circuit may receive and/or send electronic signals to perform one or more functions described in the present disclosure.

The storage device 130 may be configured to store data and/or instructions related to determining the arrhythmia type of an electrocardiogram signal. For example, the storage device 130 may store data and/or instructions that the server 120 may execute or use to perform exemplary methods described in the present disclosure. In some embodiments, the storage device 130 may include a mass storage, removable storage, a volatile read-and-write memory, a read-only memory (ROM), or the like, or a combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or a combination thereof.

In some embodiments, the storage device 130 may be connected to the network 150 to communicate with one or more components in the system 100 (e.g., the ECG machine 110, the server 120, the user terminal 160). One or more components in the system 100 may access the data or instructions stored in the storage device 130 via the network 150. In some embodiments, the storage device 130 may be directly connected to or communicate with one or more components in the system 100 (e.g., the ECG machine 110, the server 120, the user terminal 160). In some embodiments, the storage device 130 may be part of the server 120.

The information source 140 may be a source configured to provide other information for the system 100. The information source 140 may provide the system 100 with information of one or more patients, for example, medical history, medical records, physical characteristics, other body examination results, or the like, or a combination thereof. The information source 140 may be implemented in a single central server, multiple servers connected via a communication link, or multiple personal devices. When the information source 140 is implemented in multiple distributed devices, the distributed devices can generate content (e.g., as referred to as the "patient records"), for example, by uploading text, voice, image and/or video to a cloud server. An information source may be generated by the multiple distributed devices and the cloud server.

The network 150 may facilitate exchange of information and/or data. In some embodiments, one or more components in the system 100 (e.g., the ECG machine 110, the server 120, the storage device 130, the information source 140, and the user terminal 160) may send and/or receive information and/or data to/from other component(s) in the system 100 via the network 150. For example, the server 120 may obtain and/or acquire information (e.g., patient records) from the ECG machine 110 via the network 150. As another example, the server 120 may send analysis result (e.g., a prediction arrhythmia type of an electrocardiogram signal) to the user terminal 160 via the network 150. In some embodiments, the network 150 may be any type of wired or wireless network, or combination thereof. Merely by way of example, the network 150 may include a cable network, a wireline network, an optical fiber network, a tele communications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, a global system for mobile communications (GSM) network, a code-division multiple access (CDMA) network, a time-division multiple access (TDMA) network, a general packet radio service (GPRS) network, an enhanced data rate for GSM evolution (EDGE) network, a wideband code division multiple access (WCDMA) network, a high speed downlink packet access (HSDPA) network, a long term evolution (LTE) network, a user datagram protocol (UDP) network, a transmission control protocol/Internet protocol (TCP/IP) network, a short message service (SMS) network, a wireless application protocol (WAP) network, a ultra wide band (UWB) network, an infrared ray, or the like, or a combination thereof. In some embodiments, the system 100 may include one or more network access points. For example, the system 100 may include wired or wireless network access points such as base stations and/or wireless access points, through which one or more components of the system 100 may be connected to the network 150 to exchange data and/or information.

In some embodiments, the user terminal 160 may be an individual, a tool or other entity to present information about one or more patients (e.g., an examination result, a medical image) to a user. The user of the user terminal 160 may be a patient, a doctor, a medical examiner, a nurse, a researcher, or the like, or a combination thereof. In some embodiments, the user terminal 160 may be a device that configured to examine a patient to obtain ECG of the patient. For example, the user terminal 160 may be a wearable device including electrodes for obtaining ECG signals. In some embodiments, the user terminal 160 may include a mobile device 160-1, a laptop computer 160-2, a desktop computer 160-3, or the like, or a combination thereof. In some embodiments, the mobile device 160-1 may include a smart home device, a wearable device, a smart mobile device, a virtual reality device, an augmented reality device, or the like, or a combination thereof. In some embodiments, the smart home device may include a smart lighting device, a control device of an intelligent electrical apparatus, a smart monitoring device, a smart television, a smart video camera, an interphone, or the like, or a combination thereof. In some embodiments, the wearable device may include a smart bracelet, a smart footgear, a smart glass, a smart helmet, a smartwatch, a smart clothing, a smart backpack, a smart accessory, or the like, or a combination thereof. In some embodiments, the smart mobile device may include a smartphone, a personal digital assistant (PDA), a gaming device, a navigation device, a point of sale (POS) device, or the like, or a combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or a combination thereof. For example, the virtual reality device and/or the augmented reality device may include a Google Glass, an Oculus Rift, a HoloLens, a Gear VR, etc.

Figure 2:
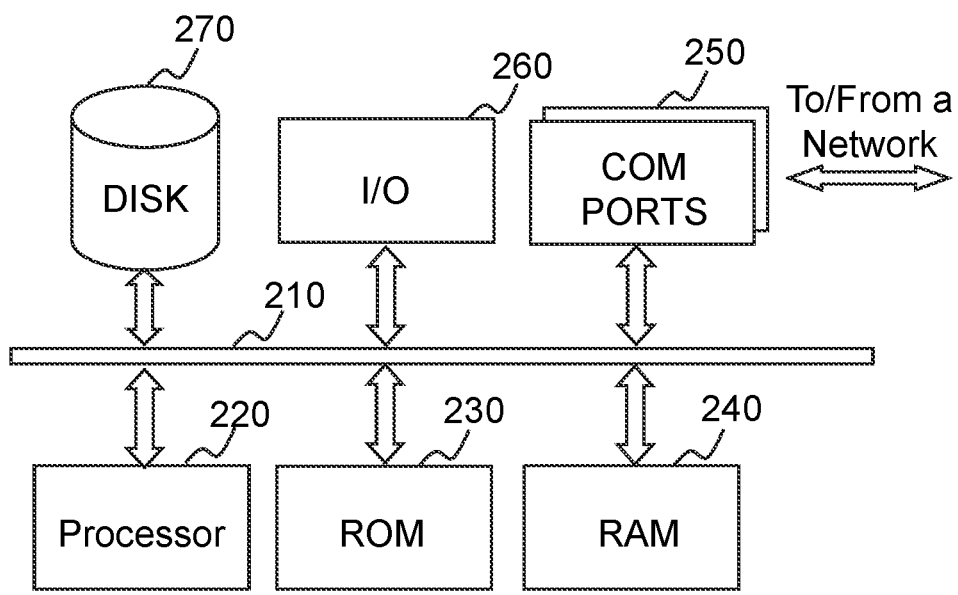
FIG. 2 is a schematic diagram illustrating exemplary hardware and/or software components of a computing device according to some embodiments of the present disclosure.

FIG. 2 is a schematic diagram illustrating exemplary hardware and software components of a computing device 200 on which the server 120, the storage device 130, the user terminal 160 and/or the information source 140 may be implemented according to some embodiments of the present disclosure. The particular system may use a functional block diagram to explain the hardware platform containing one or more user interfaces. The computer may be a computer with general or specific functions. Both types of the computers may be configured to implement any particular system according to some embodiments of the present disclosure. Computing device 200 may be configured to implement any components that perform one or more functions disclosed in the present disclosure. For example, the computing device 200 may implement any component of the system 100 as described herein. In FIGS. 1-2, only one such computer device is shown purely for convenience purposes. One of ordinary skill in the art would understand at the time of filing of this application that the computer functions relating to the on-demand service as described herein may be implemented in a distributed fashion on a number of similar platforms, to distribute the processing load.

The computing device 200, for example, may include COM ports 250 connected to and from a network connected thereto to facilitate data communications. The computing device 200 may also include a processor (e.g., the processor 220), in the form of one or more processors (e.g., logic circuits), for executing program instructions. For example, the processor may include interface circuits and processing circuits therein. The interface circuits may be configured to receive electronic signals from a bus 210, wherein the electronic signals encode structured data and/or instructions for the processing circuits to process. The processing circuits may conduct logic calculations, and then determine a conclusion, a result, and/or an instruction encoded as electronic signals. Then the interface circuits may send out the electronic signals from the processing circuits via the bus 210.

The exemplary computing device may include the internal communication bus 210, program storage and data storage of different forms including, for example, a disk 270, and a read-only memory (ROM) 230, or a random access memory (RAM) 240, for various data files to be processed and/or transmitted by the computing device. The exemplary computing device may also include program instructions stored in the ROM 230, RAM 240, and/or another type of non-transitory storage medium to be executed by the processor 220. The methods and/or processes of the present disclosure may be implemented as the program instructions. The computing device 200 also includes an I/O component 260, supporting input/output between the computer and other components. The computing device 200 may also receive programming and data via network communications.

Merely for illustration, only one processor 220 is illustrated in FIG. 2. Multiple processors are also contemplated; thus operations and/or method steps performed by one processor as described in the present disclosure may also be jointly or separately performed by the multiple processors. For example, if in the present disclosure the processor 220 of the computing device 200 executes both step A and step B, it should be understood that step A and step B may also be performed by two different processors jointly or separately in the computing device 200 (e.g., the first processor executes step A and the second processor executes step B, or the first and second processors jointly execute steps A and B).

Figure 3:
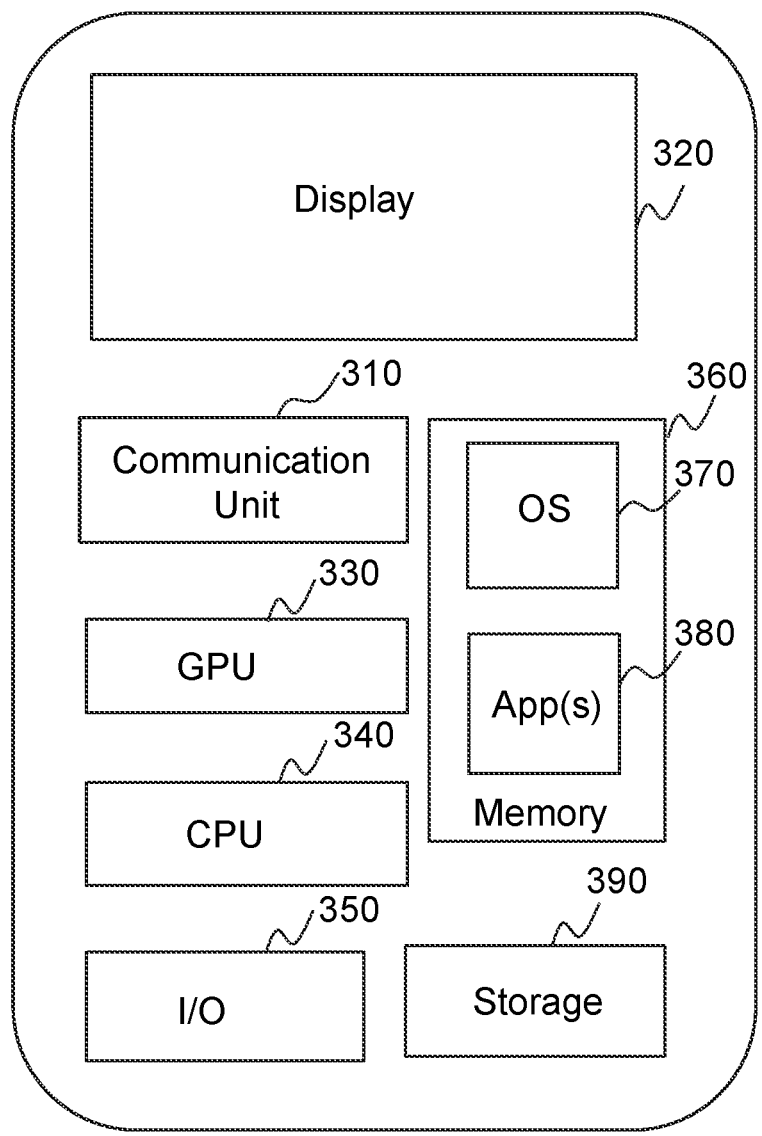
FIG. 3 is schematic diagram illustrating exemplary hardware and/or software components of a mobile device according to some embodiments of the present disclosure.

FIG. 3 is a schematic diagram illustrating exemplary hardware and/or software components of an exemplary mobile device on which the user terminal 160 may be implemented according to some embodiments of the present disclosure. As illustrated in FIG. 3, the mobile device 300 may include a communication unit 310, a display 320, a graphics processing unit (GPU) 330, a central processing unit (CPU) 340, an I/O 350, a memory 360, and a storage 390. The CPU 340 may include interface circuits and processing circuits similar to the processor 220. In some embodiments, any other suitable component, including but not limited to a system bus or a controller (not shown), may also be included in the mobile device 300. In some embodiments, a mobile operating system 370 (e.g., iOS™, ANDROID™, Windows Phone™) and one or more applications 380 may be loaded into the memory 360 from the storage 390 in order to be executed by the CPU 340. The applications 380 may include a browser or any other suitable mobile apps for receiving and rendering information relating to a service request or other information from the location-based service providing system on the mobile device 300. User interactions with the information stream may be achieved via the I/O devices 350 and provided to the server 120 and/or other components of the system 100 via the network 150.

In order to implement various modules, units and their functions described above, a computer hardware platform may be used as hardware platforms of one or more elements (e.g., a module of the server 120 described in FIG. 2). Since these hardware elements, operating systems, and program languages are common, it may be assumed that persons skilled in the art may be familiar with these techniques and they may be able to provide information required in the route planning according to the techniques described in the present disclosure. A computer with a user interface may be used as a personal computer (PC), or other types of workstations or terminal devices. After being properly programmed, a computer with a user interface may be used as a server. It may be considered that those skilled in the art may also be familiar with such structures, programs, or general operations of this type of computer device. Thus, extra explanations are not described for the figures.

Figure 4:
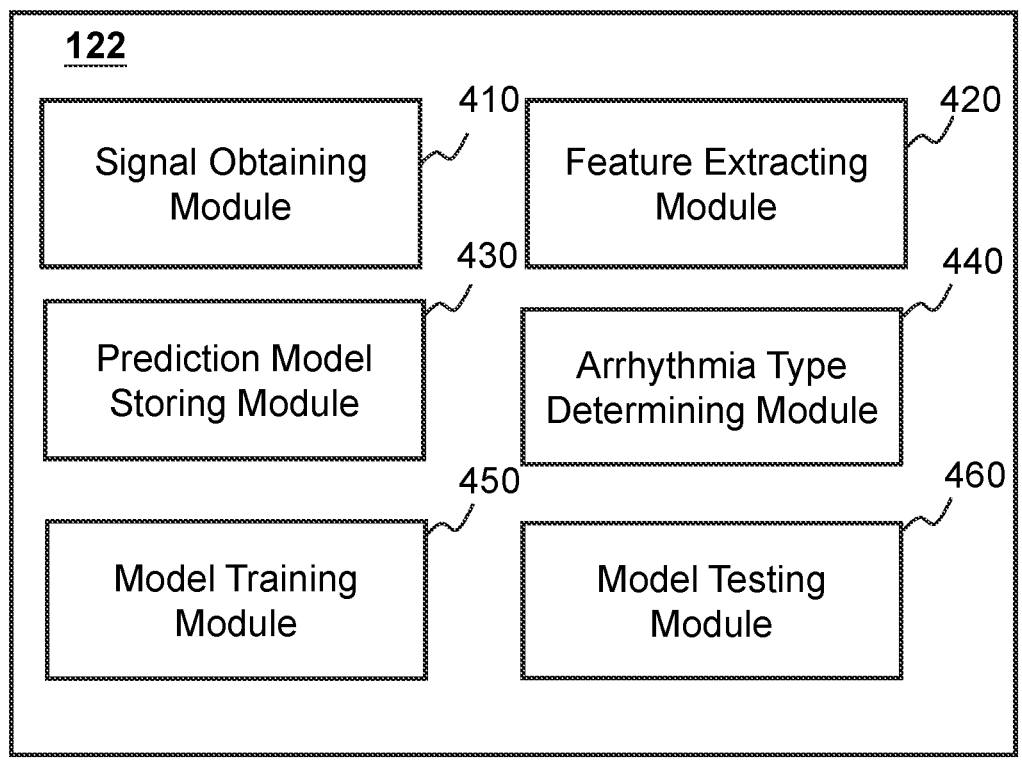
FIG. 4 is a block diagram illustrating an exemplary processing engine according to some embodiments of the present disclosure.

FIG. 4 is a block diagram illustrating an exemplary processing engine 122 according to some embodiments of the present invention. The processing engine 122 may include a signal obtaining module 410, a feature extracting module 420, a prediction model obtaining module 430, an arrhythmia type determining module 440, a model training module 450, and a model testing module 460. Each, part, or all of the modules may be hardware circuits of all or part of the processing engine 122. Each, part, or all of the modules may also be implemented as an application, or a set of instructions read and executed by the processing engine 122. Further, the modules may be a combination of the hardware circuits and the application/instructions. For example, the modules may be the part of the processing engine 122 when the processing engine is executing the application/set of instructions.

The signal obtaining module 410 may be configured to obtain an ECG signal. For example, the signal obtaining module 410 may first obtain an original ECG signal of a patient from an ECG machine 110, and preprocess the original ECG signal (e.g., filter the original ECG signal) to obtain the ECG signal to be determined. As another example, the signal obtaining module 410 may obtain the ECG signal that to be determined from storage (e.g., the storage device 130, the ROM 230, the RAM 240) in the system 100.

The feature extracting module 420 may be configured to extract or obtain a feature vector of the ECG signal. In some embodiments, the feature extracting module 420 may process the ECG signal to obtain the feature vector. The feature vector may include a threshold crossing sample (TCSC) percent feature, an L-Z complexity feature, an empirical mode decomposition (EMD) complex number feature, a sample entropy feature, a set of wavelet transform energy features, or the like, or a combination thereof. For example, the feature extracting module 420 may obtain a TCSC percent feature by applying an TCSC algorithm on the ECG signal, an L-Z complexity feature by applying an L-Z Complexity Measure Algorithm on the ECG signal, a EMD complex number feature by applying an EMD algorithm on the ECG signal, a sample entropy feature by applying a sample entropy algorithm on the ECG signal, a set of wavelet transform energy features by applying a wavelet transform algorithm on the ECG signal, or the like, or a combination thereof. Detail descriptions of the feature extracting module 420 may be found elsewhere in the present disclosure (e.g., FIG. 7 and the description thereof).

The prediction model obtaining module 430 may be configured to obtain a trained prediction model. The trained prediction model may include an algorithm and/or method for predicting an arrhythmia type of an ECG signal. In some embodiments, the prediction model obtaining module 430 may obtain the trained prediction model from storage (e.g., the storage device 130, the ROM 230, the RAM 240) in the system 100. In some embodiments, the prediction model obtaining module 430 may obtain the trained prediction model from the model training module 450 after training a preliminary prediction model or an intermediate prediction model.

The arrhythmia type determining module 440 may be configured to determine an arrhythmia type of ECG signal. The arrhythmia type may include a Ventricular Fibrillation (VF), a Ventricular Tachycardia (VT), a Ventricular Flutter (VFL), a Supraventricular tachycardia (SVT), extra beats, ventricular arrhythmias, brad arrhythmias, or the like, or a combination thereof. In some embodiments, the arrhythmia type determining module 440 may determine the arrhythmia type of the ECG signal based on the trained prediction model (e.g., obtained from the prediction model obtaining module 430) and the feature vector (e.g., obtained from the feature extracting module 420). For example, the arrhythmia type determining module 440 may input the feature vector and/or the ECG signal into the trained prediction model, and the output of the trained prediction model may include the arrhythmia type of the ECG signal.

The model training module 450 may be configured to train a model (e.g., a preliminary prediction model, an intermediate prediction model) to obtain a trained model (e.g., a trained prediction model, an intermediate prediction model). For example, the model training module 450 may obtain training samples and the feature vectors of the training samples, and train a preliminary prediction model by inputting the training samples and/or the feature vectors into the preliminary prediction model to obtain a trained prediction model. As another example, the model training module 450 may train a preliminary prediction model by inputting the training samples and/or the feature vectors into the preliminary prediction model to obtain an intermediate prediction model. As still another example, the model training module 450 may re-train a new preliminary prediction model to obtain the trained prediction model. Detail descriptions of the model training module 450 may be found elsewhere in the present disclosure (e.g., FIG. 7 and FIG. 8 and the descriptions thereof).

The model testing module 460 may be configured to test the intermediate prediction model to determine whether to obtain the trained prediction model. In some embodiments, the model testing module 460 may obtain testing samples and the feature vectors thereof, and input the testing samples and/or the feature vectors into the intermediate prediction model to determine an accuracy rate of the intermediate prediction model. The model testing module 460 may determine the accuracy rate by comparing the outputs from the intermediate prediction model and known arrhythmia types of the corresponding testing samples. In some embodiments, the model testing module 460 may compare the accuracy rate with an accuracy threshold to determine whether to designate the intermediate prediction model as the trained prediction model or to re-train the intermediate prediction model. Detail descriptions of the model testing module 460 may be found elsewhere in the present disclosure (e.g., FIG. 8 and the description thereof).

The modules in the processing engine 122 may be connected to or communicate with each other via a wired connection or a wireless connection. The wired connection may include a metal cable, an optical cable, a hybrid cable, or the like, or a combination thereof. The wireless connection may include a Local Area Network (LAN), a Wide Area Network (WAN), a Bluetooth™, a ZigBee™, a Near Field Communication (NFC), or the like, or a combination thereof. Two or more of the modules may be combined as a single module, and any one of the modules may be divided into two or more units. For example, the model training module 450 may be integrated into the model testing module 460 as a single module that may both train and test the intermediate models to obtain a trained prediction model. As another example, the feature extracting module 420 may be divided into two or more units, for example, a first feature extracting unit, a second feature extracting unit, a third feature extracting unit, a fourth feature extracting unit, and a fifth feature extracting unit, which work together to implement the functions (e.g., extract five features respectively) of the feature extracting module 420, respectively.

Figure 5:
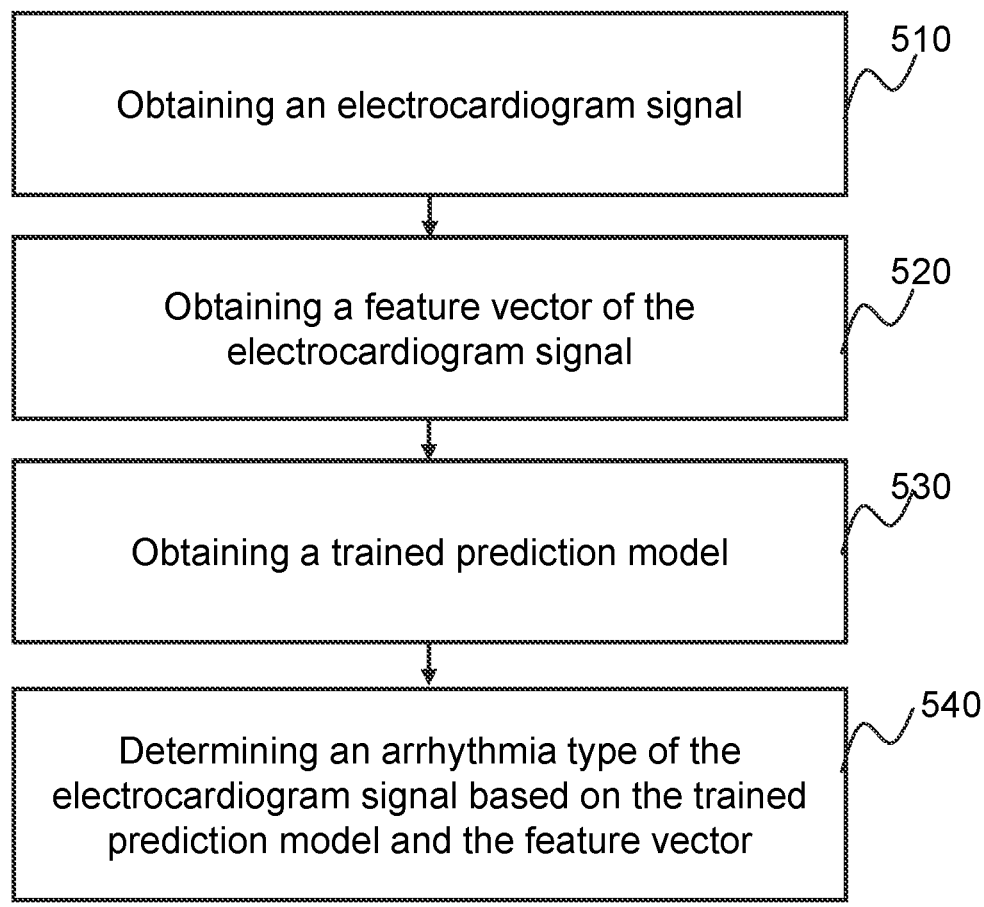
FIG. 5 is a flowchart illustrating an exemplary process and/or method for determining an arrhythmia type according to some embodiments of the present disclosure.

FIG. 5 is a flowchart of an exemplary process and/or method for determining an arrhythmia type according to some embodiments of the present disclosure. In some embodiments, one or more steps in the process 500 may be implemented in the system 100 illustrated in FIG. 1. For example, one or more steps in the process 500 may be stored in the storage (e.g., the storage device 130, the ROM 230, the RAM 240) as a form of instructions, and invoked and/or executed by the server 120 (e.g., the processing engine 122 in the server 120, or the processor 220 of the processing engine 122 in the server 120).

In 510, the processor 220 (or the signal obtaining module 410) may obtain an ECG signal. In some embodiments, the processor 220 may obtain the ECG signal after preprocessing an original ECG signal. For example, the processor 220 may filter the original ECG signal to remove noises (or at least a portion thereof) and/or depress drifts of the original ECG signal. In some embodiments, the original ECG signal may be obtained from the ECG machine 110 or the storage device 130. In some embodiments, the ECG signal may include a segment of the original ECG signal. For example, the ECG signal may be a segment of an original ECG signal, and the segment may last several seconds. For instance, the ECG signal may be an eight-second segment of the original ECG signal. The processor 220 may extract an eight-second signal segment from the original ECG signal and preprocess the extracted signal segment to obtain the ECG signal (by, for example, removing at least some noise from the segment).

In 520, the processor 220 (or the feature extracting module 420) may obtain (or extract) a feature vector of the obtained ECG signal.

In some embodiments, the feature vector may include a plurality of features extracted from the ECG signal. For example, the feature vector may include a threshold crossing sample (TCSC) percent feature, an L-Z complexity feature, an empirical mode decomposition (EMD) complex number feature, a sample entropy feature, a set of wavelet transform energy features, or the like, or a combination thereof.

The TCSC percent feature used herein refers to a percentage value of the number of samples in the ECG signal that are greater than a number threshold according to a threshold crossing sample algorithm (TCSC algorithm). For example, the processor 220 may implement one or more following steps on the ECG signal obtained in 510 to obtain the TCSC percent feature $N_a$.

Step 1A: The feature extracting module 420 may divide the ECG signal into several segments (e.g., each segment includes three seconds of the ECG signal), and multiply each segment by a cosine function $\varphi(t)$ as follows:

$$\varphi(t) = \begin{cases} \frac{1}{2}(1-\cos(4\pi t)) & 0 \le t \le \frac{1}{4} \\ 1 & \frac{1}{4} \le t \le L_s - \frac{1}{4} \\ \frac{1}{2}(1-\cos(4\pi t)) & L_s - \frac{1}{4} \le t \le L_s \end{cases} \quad (1)$$

wherein t denotes the time in the ECG signal, and $L_s$ denotes the time length of a segment (e.g., $L_s$ may be three seconds).

Step 2A: The feature extracting module 420 may normalize the product of the ECG signal and the cosine function $\varphi(t)$. For example, the feature extracting module 420 may determine (or calculate) the greatest absolute value of the product of the ECG signal and the cosine function $\varphi(t)$, and divide the product of the ECG signal and the cosine function $\varphi(t)$ by the greatest absolute value thereof to obtain a normalized signal.

Step 3A: The feature extracting module 420 may sample the normalized signal to obtain a plurality of sampling points $x_i (i=1, 2, 3, \ldots, n)$, wherein n is the number of the sampling points. For example, the feature extracting module 420 may obtain a sampling point every $L_s/n$ seconds from the normalized signal to obtain the plurality of sampling points ($L_s$ denotes the length of the normalized signal). As another example, the feature extracting module 420 may randomly select n sampling points from the normalized signal to obtain the plurality of sampling points. The feature extracting module 420 may compare the value of each sampling point with a threshold $V_0$ to obtain a binary character string $b=\{b_1 b_2 \ldots b_n\}$. For example, if $x_i > V_0$, $b_i=1$; otherwise, $b_i=0$.

Step 4A: The feature extracting module 420 may determine the number of value 1 in the binary character string $b=\{b_1 b_2 \ldots b_n\}$ to obtain the number of the sampling points that are greater than the threshold $V_0$ (which is denoted as $n_0$ herein). The feature extracting module 420 may then determine N:

$$N = \frac{n_0}{n} \times 100, \quad (2)$$

wherein n denotes the total number of the sampling points. N may indicate the ratio of the sampling points that are greater than the threshold $V_0$ over all samples in the segment.

Step 5A: The feature extracting module 420 may determine the average value of the N values of the segments of the ECG signal. For example, if the length of the ECG signal is $L_e$ seconds, wherein $L_e$ is greater than 3 seconds (Le>3), the feature extracting module 420 may determine an N every three seconds, each segment may slide once per second, and the total number of continuous segments (the length of each segment is three second) is Le−2. The average value $N_a$ (which also refers to as the TCSC percent feature) of Le−2 segments may be determined as follows:

$$N_a = \frac{1}{L_e - 2} \sum_{i=1}^{L_e - 2} N_i, \quad (3)$$

wherein $N_i$ denotes a value N of the $i_{th}$ segment with the length of three seconds.

The L-Z complexity feature may refer to a complexity value determined according to an L-Z Complexity Measure Algorithm. For example, the processor 220 may implement one or more following steps on the ECG signal obtained in 510 to obtain the L-Z complexity feature C(n).

Step 1B: The feature extracting module 420 may sample the ECG signal to obtain a plurality of sampling points $X=\{x_1, x_2, \ldots, x_n\}$, wherein n is the number of the sampling points. For example, the feature extracting module 420 may obtain a sampling point every $L_e/n$ seconds from the ECG signal to obtain the plurality of sampling points ($L_e$ denotes the length of the ECG signal). As another example, the feature extracting module 420 may randomly select n sampling points from the ECG signal to obtain the plurality of sampling points. The feature extracting module 420 may determine an average value $x_m$ of the sampling points and subtract the average value $x_m$ from each sampling point value to obtain a new signal sequence: $X_{new}=\{x_{new1}, x_{new2}, \ldots, x_{newn}\}$.

Step 2B: The feature extracting module 420 may obtain a positive peak $V_p$ and a negative peak $V_n$ of the new signal sequence. The positive peak $V_p$ may refer to the positive maximum value among a plurality of strength values of the signals in the new signal sequence. The negative peak $V_n$ may refer to the negative minimum value among the plurality of strength values of the signals in the new signal sequence. In some embodiments, the feature extracting module 420 determine each strength value of each signal in the new signal sequence. The positive maximum value may be selected as the positive peak $V_p$, and the negative minimum value may be selected as the negative peak $V_n$. The feature extracting module 420 may determine the number of the new sampling points in the new signal sequence that have the value within a range relating to the positive peak $V_p$ (e.g., the range of $0<x_i<0.1*V_p$), which is denoted herein as $P_c$. The feature extracting module 420 may also determine the number $N_c$ of the new sampling points (in the new signal sequence) that has the value in a range relating to the negative peak $V_n$ (e.g., $0.1* V_n<x_i<0$).

The feature extracting module 420 may determine a threshold $T_d$ based on the $P_c$ and $N_c$. For example, if $P_c+N_c<0.4n$, the threshold $T_d=0$; if $P_c<N_c$, the threshold $T_d=0.2*V_p$; otherwise, the threshold $T_d=0.2*V_n$.

Step 3B: The feature extracting module 420 may compare the value of $x_i$ with the threshold $T_d$ to obtain a binary character string of $\{s_1 s_2 \ldots s_n\}$. For example, if $x_i<T_d$, $s_i=0$; otherwise, $s_i=1$.

Definitions of several character string: S and Q denote two character strings. SQ may denote a merging string of S and Q. For example, the character string SQ may refer to a character string including all characters in the character string Q and all characters in the character string S, and the first character of the character string Q is after the last character of the character string S. $SQ_{TT}$ denotes a character string obtained by removing the last character from the character string SQ; and $v(SQ_{TT})$ denotes a set of all different substrings of the character string $SQ_{TT}$. A substring refers to a string of any number of consecutive character in the character string $v(SQ_{TT})$. The character string $v(SQ_{TT})$ may include at least two substrings that are the same. A different substring refers to a string among all the substrings of the character string $v(SQ_{TT})$ that is different from any other substrings. For example, all substrings of the character string $SQ_{TT}$ may be extracted from the character string $SQ_{TT}$. $v(SQ_{TT})$ refers to a collection of substrings that removes all the same substrings from the extracted substrings. In the beginning, the feature extracting module 420 may define $c(n)=1$, $S=s_1$, $Q=s_2$, so $SQ\pi=s_1$. Assume that $S=s_1s_2 \ldots s_r$, $Q=s_{r+1}$; if $Q \in \upsilon(SQ\pi)$, $s_{r+1}$ is a substring of $s_1s_2 \ldots s_r$, so S remains unchanged.

Step 4B: Q may be updated to $Q=s_{r+1}s_{r+2}$. The feature extracting module 420 may determine whether $Q \in \upsilon(SQ\pi)$. This determination operation may stop until $Q \notin \upsilon(SQ\pi)$, and then $Q=s_{r+1}s_{r+2} \ldots s_{r+i}$. Q is not a substring of $s_1s_2 \ldots s_r$, and the feature extracting module 420 may add 1 to c(n).

Step 5B: S and Q may be merged, forming a new S: $S=s_1s_2 \ldots s_r s_{r+1} \ldots s_r$, and and $Q=s_{r+i+1}$.

Step 6B: Repeat steps 4B and 5B until Q includes the last character and the value of c(n) is the number of different substrings in $s_1, s_2, \ldots, s_n$. The feature extracting module 420 may normalize c(n) to obtain the L-Z complexity feature C(n):

$$C(n) = \frac{c(n)}{b(n)}, \tag{4}$$

wherein b(n) denotes a gradual behavior of a random string $$\left( e.g., b(n) = \frac{n}{\log_2 n} \right).$$

The EMD complex number feature may refer to a complex number determined according to an EMD algorithm. For example, the processor 220 may implement one or more following steps on the ECG signal obtained to obtain the EMD complex number feature z.

Step 1C: The ECG signal (denoted as $x_i(n)$), which has a time length of $L_e$, may be divided into a plurality of segments. The ECG signal may have a time length of $L_e$, and each of the segments may have a time length $L_a$, where Step 2C: The feature extracting module 420 may apply an EMD algorithm to $x_i(n)$:

$$x_i(n) = imf_{1i}(n) + imf_{2i}(n) + r_i(n) \tag{5},$$

wherein $imf_{1i}(n)$ is a first intrinsic mode function (IMF) of $x_i(n)$ according to the EMD algorithm; $imf_{2i}(n)$ is a second IMF of $x_i(n)$ according to the EMD algorithm; and $r_i(n)$ is the remnant of $x_i(n)$ according to the EMD algorithm.

Step 3C: The feature extracting module 420 may determine the level of noise $V_n$ of $x_i(n)$:

$$V_n = \alpha \times \max\{x_i(n)\} \tag{6},$$

wherein max $\{x_i(n)\}$ is the maximum value of $x_i(n)$, and a is a predetermined constant.

Step 4C: The feature extracting module 420 may determine the number $n_L$ of amplitudes in the $imf_{1i}(n)$ that are between $-V_n$ and $V_n$ ($[-V_n, V_n]$, which also refers to being exceeding the level of noise $V_n$):

$$|imf_{1i}(n_L)| \leq V_n \tag{7},$$

Step 5C: The feature extracting module 420 may determine a ratio L of the sum of squares of the amplitudes of the $f_{1i}(n)$ that exceeds the level of noise $V_n$ (the number of the $imf_{1i}(n)$ is $n_L$) to the sum of squares of the amplitudes of the signal $x_i(n)$ as follows:

$$L = \frac{\sum_{n \in n_L} imf_{1i}^2(n)}{\sum_{n \in n_L} x_i^2(n)}, \tag{8}$$

Step 6C: The feature extracting module 420 may determine a proper IMF $imf_i(n)$ based on the ration L:

$$imf_i(n) = \begin{cases} imf_{1i}(n) + imf_{2i}(n), & L \leq \beta \\ imf_{1i}(n), & \text{Otherwise} \end{cases}, \tag{9}$$

wherein β is a predetermined constant.

Step 7C: The feature extracting module 420 may determine an angle $\theta_{<x_i, imf_i>}$ between $x_i$ and $imf_i$:

$$\theta_{<x_i, imf_i>} = \cos^{-1} \frac{imf_i^T \times x_i}{\|imf_i\| \|x_i\|}, \tag{10}$$

wherein $x_i = [x_i(0) x_i(1) \ldots x_i(N-1)]^T$, $imf_i = [imf_i(0) imf_i(1) \ldots imf_i(N-1)]^T$; $\|.\|$ denotes an Euclidean norm of a vector; and T denotes a transpose of a matrix. The feature extracting module 420 may also determine an angel $\theta_{<x_i, r_i>}$ between $x_i$ and $r_i$ according to the same method, wherein $r_i = [r_i(0) r_i(1) \ldots r_i(N-1)]^T$.

Step 8C: The feature extracting module 420 may determine an average angle value $\theta_{<x_i, imf_i>}^\alpha$ of the $L_e$ ECG signal:

$$\theta_{<x, imf>}^a = \frac{1}{L_e - L_a + 1} \sum_{i=1}^{L_e - L_a + 1} \theta_{<x_i, imf_i>}, \tag{11}$$

and the feature extracting module 420 may also determine an average angle value $\theta_{<x, r>}^\alpha$ of $\theta_{<x_i, r_i>}$ according to the same method.

Step 9C: The feature extracting module 420 may determine a complex number z (also refers to as the EMD complex number feature) based on average angels $\theta_{<x_i, imf_i>}^{\alpha}$ and $\theta_{<x, r>}^{\alpha}$:

$$z = \theta_{<x, imf>}^a + j\left(-\frac{\pi}{2} - \theta_{<x, r>}^a\right). \tag{12}$$

The sample entropy feature may refer to a value determined based on the obtained ECG signal according to a sample entropy algorithm. For example, the processor 220 may implement one or more following steps on the ECG signal to obtain the sample entropy feature, which is denoted herein as SampEn(m, r, N).

Step 1D: The feature extracting module 420 may sample the ECG signal to obtain N sampling points of $\{u_1, u_2, \ldots, u_n\}$. For example, the feature extracting module 420 may obtain a sampling point every $L_s/N$ seconds from the ECG signal to obtain the plurality of sampling points ($L_s$ denotes the length of the ECG signal). As another example, the feature extracting module 420 may randomly select n sampling points from the ECG signal to obtain the plurality of sampling points.

Step 2D: The feature extracting module 420 may generate a group of m-dimensional vectors (from Xm(1) to Xm(N-m)) in sequence of the number of the sampling points, where $Xm(i) = \{u(i), u(i+m-1)\}$, and $i = 1 \sim N-m$. Xm(i) is m sampling points from the sampling point i.

Step 3D: The feature extracting module 420 may designate the distance d[Xm(i), Xm(j)] between two vectors, Xm(i) and Xm(j), as the maximum difference value between two corresponding elements:

$$d[Xm(i), Xm(j)] = \max(|u(i+k) - u(j+k)|) \tag{13},$$

where $k = 0 \sim m-1$; $i, j = 1 \sim N-m$, and $j \neq i$.

Step 4D: The feature extracting module 420 may compare i with N−m. If feature extracting module 420 determines that i≤N−m, the feature extracting module 420 may determine the values in d[Xm(i), Xm(j)] that are less than a predetermined threshold (denoted as r) and the number $N^m(i)$ of such values. The feature extracting module 420 may also determine a ration $B_r^m(i)$ of the number $N^m(i)$ to the total distance number N−m−1 as follows:

$$B_r^m(i)=N^m(i)/(N-m-1) \quad (14),$$

and the average value $B^m(r)$ of all $B_r^m(i)$:

$$B^m(r)=(N-m)^{-1}\Sigma_{i=1}^{N-m} B_r^m(i) \quad (15),$$

where N−m donates the total number of the $B_r^m(i)$.

Step 5D: The feature extracting module 420 may increase m by 1 (i.e., m+1), and implement step 2D~Step 4D to obtain the average value $B^{m+1}(r)$ of all $B_r^{m+1}(i)$ as follows:

$$B^{m+1}(r)=(N-m)^{-1}\Sigma_{i=1}^{H-m} B_r^{m+1}(i) \quad (16).$$

Step 6D: The feature extracting module 420 may determine a theoretical sample entropy SampEn(m, r) of the sequence:

$$SampEn(m, r) = \lim_{N \to \infty} \{-\ln[B^{m+1}(r)/B^m(r)]\}, \quad (17)$$

when N is a limited value, the estimated sample entropy SampEn(m,r,N) (also refers to as the sample entropy feature) of the sequence with the length of N may be determined as follows:

$$SampEn(m,r,N)=-\ln[B^{m+1}(r)/B^m(r)] \quad (18).$$

The set of wavelet transform energy features may refer to the energy of one or more decomposed signals of the ECG signal according to a wavelet transform algorithm. In some embodiments, the processor 220 may decompose the ECG signal to obtain the set of wavelet transform energy features. For example, the feature extracting module 420 may decompose the ECG signal to several layers (e.g., seven layers) according to a wavelet transform algorithm (e.g., a wavelet base function "db4"), the energy of each layer may be D1, D2, . . . , D7. In some embodiments, the feature extracting module 420 may select at least one energy of at least one layer from the seven layers to obtain the set of wavelet transform energy features. For example, the set of wavelet transform energy feature may include energies of a layer (e.g., D3, D4, D5, D6, or D7), the frequencies of the layer are lower than the frequency of the ECG signal. As another example, the set of wavelet transform energy feature may include energies that include fewer data among the energies of the seven layers. As still another example, the set of wavelet transform energy feature may include energies that may be used to determine an arrhythmia type (e.g., using D2, D3, and D4 to determine QRS complex). In some embodiments, the feature extracting module 420 may select the energy of the fourth decomposition (D4), energy of the sixth decomposition (D6), and energy of the seventh decomposition (D7) as the set of wavelet transform energy features.

In 530, the processor 220 (or the prediction model obtaining module 430) may obtain a trained prediction model.

Figure 6A:
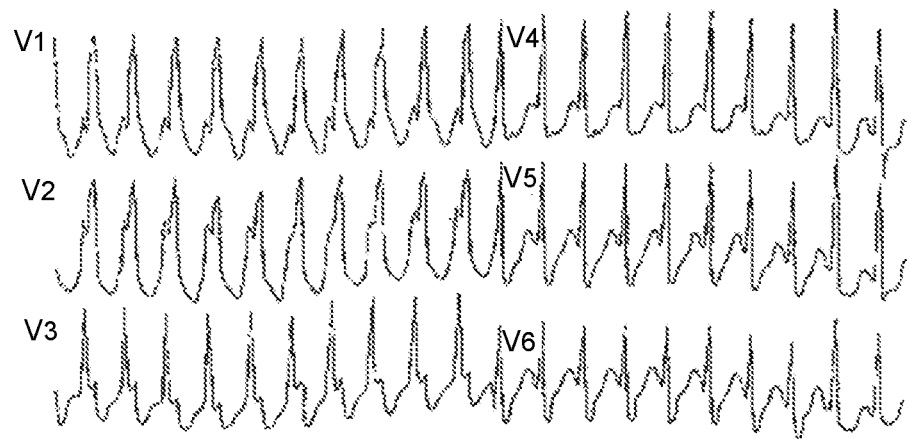
FIG. 6A is an exemplary electrocardiogram of a Supraventricular Tachycardia (SVT)
Figure 6B:
FIG. 6B is an exemplary electrocardiogram of a Ventricular Tachycardia (VT)
Figures 6C, 6D:
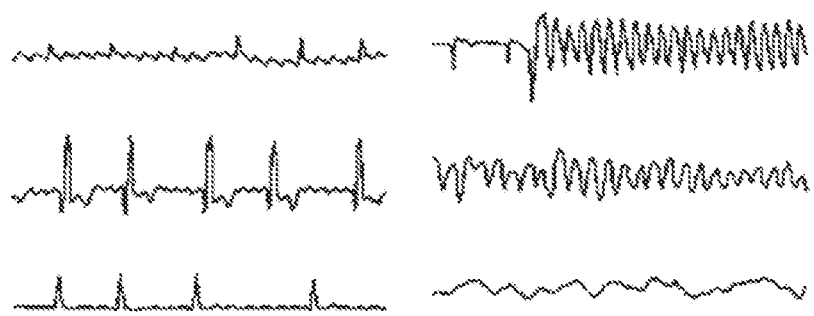
FIG. 6C is an exemplary electrocardiogram of a Ventricular Flutter (VFL)
FIG. 6D is an exemplary electrocardiogram of a Ventricular Fibrillation (VF)

In some embodiments, the trained prediction model may include an algorithm and/or method for predicting an arrhythmia type of an ECG signal. The arrhythmia type of an ECG signal may refer to an irregular performance of a heart. For example, the arrhythmia type may include a Ventricular Fibrillation (VF), a Ventricular Tachycardia (VT), a Ventricular Flutter (VFL), a Supraventricular tachycardia (SVT), extra beats, ventricular arrhythmias, brad arrhythmias, or the like, or a combination thereof. FIGS. 6A-6D illustrate four types of arrhythmia according to some embodiments of the present disclosure. FIG. 6A is an exemplary electrocardiogram of the SVT, FIG. 6B is an exemplary electrocardiogram of the VT, FIG. 6C is an exemplary electrocardiogram of the VFL, and FIG. 6D is an exemplary electrocardiogram of the VF.

In some embodiments, the processor 220 may train a preliminary prediction model to obtain the trained prediction model and store the trained prediction model into a storage device (e.g., the storage device 130, the ROM 230, the RAM 240) of the system 100. In some embodiments, the preliminary prediction model may include a classifier model, a regression model, or the like, or a combination thereof. For example, the classifier model may include a random forest model, a BP neural network model, a support vector machine (SVM) model, a wavelet neural network model, a clustering model, or the like, or a combination thereof. In some embodiments, the processor (or the device) that trains the preliminary prediction model to obtain a trained prediction model may be different from the processor (or the device) that uses the trained prediction model to predict an arrhythmia type of an ECG signal. For example, a processor of the server 120 trains the preliminary prediction model to obtain the trained prediction model, and a processor of the ECG machine 110 uses the trained model to predict the arrhythmia type of the ECG signal. The processor of the ECG machine presents the arrhythmia type to a user of the ECG machine 110. In some embodiments, the descriptions of the training of the preliminary prediction model may be found elsewhere in the present disclosure (e.g., FIG. 7 and FIG. 8 and the descriptions thereof).

In 540, the processor 220 (or the arrhythmia type determining module 440) may determine an arrhythmia type of the ECG signal based on the trained prediction model and the feature vector.

In some embodiments, the processor 220 may input the ECG signal and/or the feature vector thereof into the trained prediction model. The output of the trained prediction model may include a predicted arrhythmia type of the ECG signal. For example, the trained prediction model may be a trained random forest model, and the processor 220 may input the ECG signal, and/or at least one of the TCSC percent feature, the L-Z complexity feature, the EMD complex number feature, the sample entropy feature, and the set of wavelet transform energy features of the ECG signal into the trained random forest model. The trained random forest model may include a plurality of decision trees. The trained random forest model may output an arrhythmia type based on the votes of the plurality of decision trees based on the input to the trained random forest model. In some embodiments, each decision tree may include one vote. In some embodiments, each decision tree may include a different number of votes (e.g., a decision tree K includes two votes, a decision tree H includes one vote). In some embodiments, the trained random forest model may output an arrhythmia type that gets the most votes of the plurality of decision trees as the predicted arrhythmia type of the ECG signal.

In some embodiments, the processor 200 may determine whether the predicted arrhythmia type is one of the types that need to take a further action. For example, if the processor 220 may determine that the predicted arrhythmia type is a VF, the processor 220 may transmit an alert to a patient and/or medical staff (e.g., a doctor, a nurse) to seek further examination and/or medical assistance for the patient. The processor 220 may transmit an electronic signal including the alert via wireless communication or wire communication to a device associated with the patient and/or the medical staff. For example, the device associated with the patient and/or the medical staff may include the ECG machine 110, a monitoring equipment of the patient, a mobile terminal of the patient and/or the medical staff, a monitoring center of a hospital, or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional steps (e.g., a storing step, a preprocessing step) may be added elsewhere in the exemplary process/method 500. As another example, the obtaining the feature vector of the ECG signal may be implemented in the trained prediction model. For example, the processor 220 may only input the ECG signal into the trained prediction model, and the trained prediction model may extract the feature vector of the ECG signal and output the predicted arrhythmia type of the ECG signal.

Figure 7:
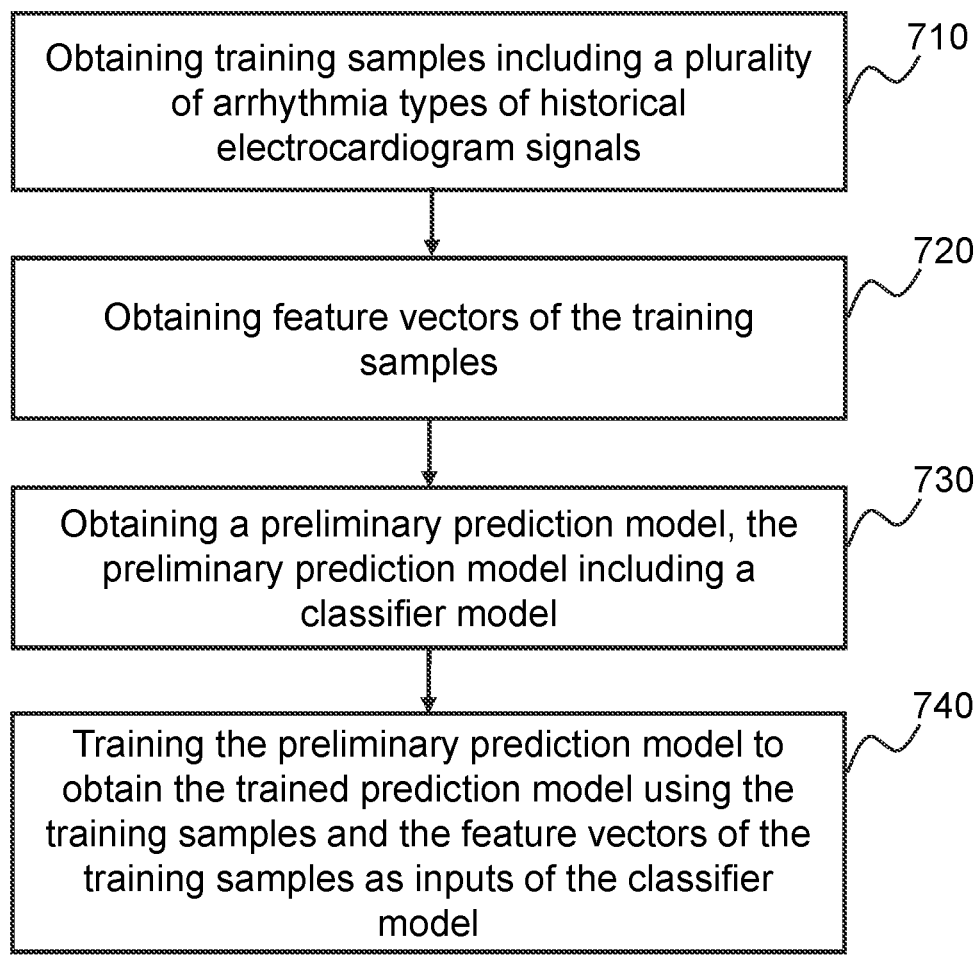
FIG. 7 is a flowchart illustrating an exemplary process and/or method of training a preliminary prediction model to obtain a trained prediction model according to some embodiments of the present disclosure.

FIG. 7 is a flowchart of an exemplary process and/or method for training a preliminary prediction model to obtain a trained prediction model according to some embodiments of the present disclosure. In some embodiments, one or more steps in the process 700 may be implemented in the system 100 illustrated in FIG. 1. For example, one or more steps in the process 700 may be stored in the storage device 130 and/or the storage (e.g., the ROM 230, the RAM 240) as a form of instructions, and invoked and/or executed by the server 120 (e.g., the processing engine 122 in the server 120, or the processor 220 of the processing engine 122 in the server 120).

In 710, the processor 220 (or the model training module 450) may obtain training samples. The training samples may include a plurality of ECG signals that the arrhythmia types thereof are known. For example, the training samples may include a plurality of ECG signals the arrhythmia types of which have already been determined. The arrhythmia types may include VT, VF, SVT, VFL, or the like, or a combination thereof.

In 720, the processor 220 (or the model training module 450) may obtain the feature vectors of the training samples.

In some embodiments, the processor 220 may extract one feature vector from one training sample. The feature vector may include a TCSC present feature, an L-Z complexity feature, an EMD complex number feature, a sample entropy feature, a set of wavelet transform energy feature, or the like, or a combination thereof. The method and/or process of obtaining the feature vector of the training samples may be found elsewhere in the present disclosure (e.g., FIG. 5 and the description thereof).

In 730, the processor 220 (or the model training module 450) may obtain a preliminary prediction model.

In some embodiments, the preliminary prediction model may refer to an initial model with initial parameters that is used for determining an algorithm and/or method for predicting the arrhythmia type of the ECG type. In some embodiments, the preliminary prediction model may include a classifier model, a regression model, etc. For example, the classifier model may include a random forest model, a BP neural network model, a support vector machine (SVM) model, a wavelet neural network model, a clustering model, or the like, or a combination thereof.

In 740, the processor 220 (or the model training module 450) may train the preliminary prediction model to obtain the trained prediction model using the training samples and the feature vectors of the training samples as the inputs of the preliminary model.

In some embodiments, the processor 220 may input the training samples and/or the feature vectors thereof into the preliminary prediction model. The initial parameters of the preliminary prediction model may be adjusted to obtain the trained prediction model.

For example, the processor 220 may input N training samples (i.e., the number of the training samples is N) and the feature vectors thereof into a random forest model. The N training samples may include four arrhythmia types including VT, SVT, VFL, and VF. The feature vector of a training sample may include M features (e.g., five features including a TCSC present feature, an L-Z complexity feature, an EMD complex number feature, a sample entropy feature and a set of wavelet transform energy feature) of each training sample. The random forest model may include a plurality of decision trees. The processor 220 may randomly select n training samples from the N training samples (or referred to the training set) according to a bootstrap sample method to train each decision tree in the random forest model. In some embodiments, the processor 220 may select m features from the M features (herein M may refer to five, and m may be an integer less than (or far less than) 5) in each feature vector to be input into each decision tree. In each decision tree, the processor 220 may further select one optimal feature from the m features that has the strongest classifying ability to split (or the most important) on each node. The processor 220 may not prune the decision tree. A plurality of decision trees may form a random forest (also refers to as the trained prediction model).

In some embodiments, the number m (i.e., the number of the features in each feature vector to be input to a decision tree) in training the random forest model may be determined based on the out-of-bag error (OBB error) method. For example, the processor 220 may obtain a plurality of OBB samples (e.g., a plurality of training samples that are not in the training set), and input the OBB samples into a plurality of decision trees (that are trained based on different feature subsets) to determine an OBB error for each decision tree. For example, there are 2/3 training samples in the training set that are used to train a particular decision tree, and the rest 1/3 training samples are used as the OBB samples to determine an OBB error of the particular decision tree. The processor 220 may input the rest 1/3 training samples into the particular decision tree to obtain a plurality of predicted result. The processor 220 may determine a number of OBB samples with the wrong predicted result. The OBB error may be a ratio of the number of OBB samples with the wrong predicted result to a total number of OBB samples. The number of features in a feature subset that has the lowest OBB error among the OBB errors may be determined as m.

In some embodiments, the optimal feature may be determined based on the importance of each feature in the m features. For example, the processor 220 may determine a first OBB error errOOB1 of each decision tree by inputting a plurality of OBB samples into each decision tree, and for each feature in each OBB sample, add a noise interference to it, and determine a second OBB error errOOB2 of each decision tree. The importance Imp of each feature may be determined based on the errOOB1, errOOB2, and the total number $N_{tree}$ of the decision tress as follows:

$$Imp = \frac{\Sigma(errOOB2 - errOOB1)}{N_{tree}}. \quad (19)$$

The higher the importance of a feature, the greater the difference after the noise interference is added. In some embodiments, the processor 220 may select a feature that has the highest importance as the optimal feature.

In some embodiments, the processor 220 may further implement a testing process on an intermediate prediction model after the training process of the preliminary prediction model (which may be a prediction model that undergo at least some training using certain training samples). The processor 220 may designate an intermediate prediction model as the trained prediction model after determining that the test result of the intermediate prediction model meet a predetermined condition. The testing the intermediate prediction model may be found elsewhere in the present disclosure (e.g., FIG. 8 and the description thereof).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional steps (e.g., a storing step, a preprocessing step) may be added elsewhere in the exemplary process/method 700.

Figure 8:
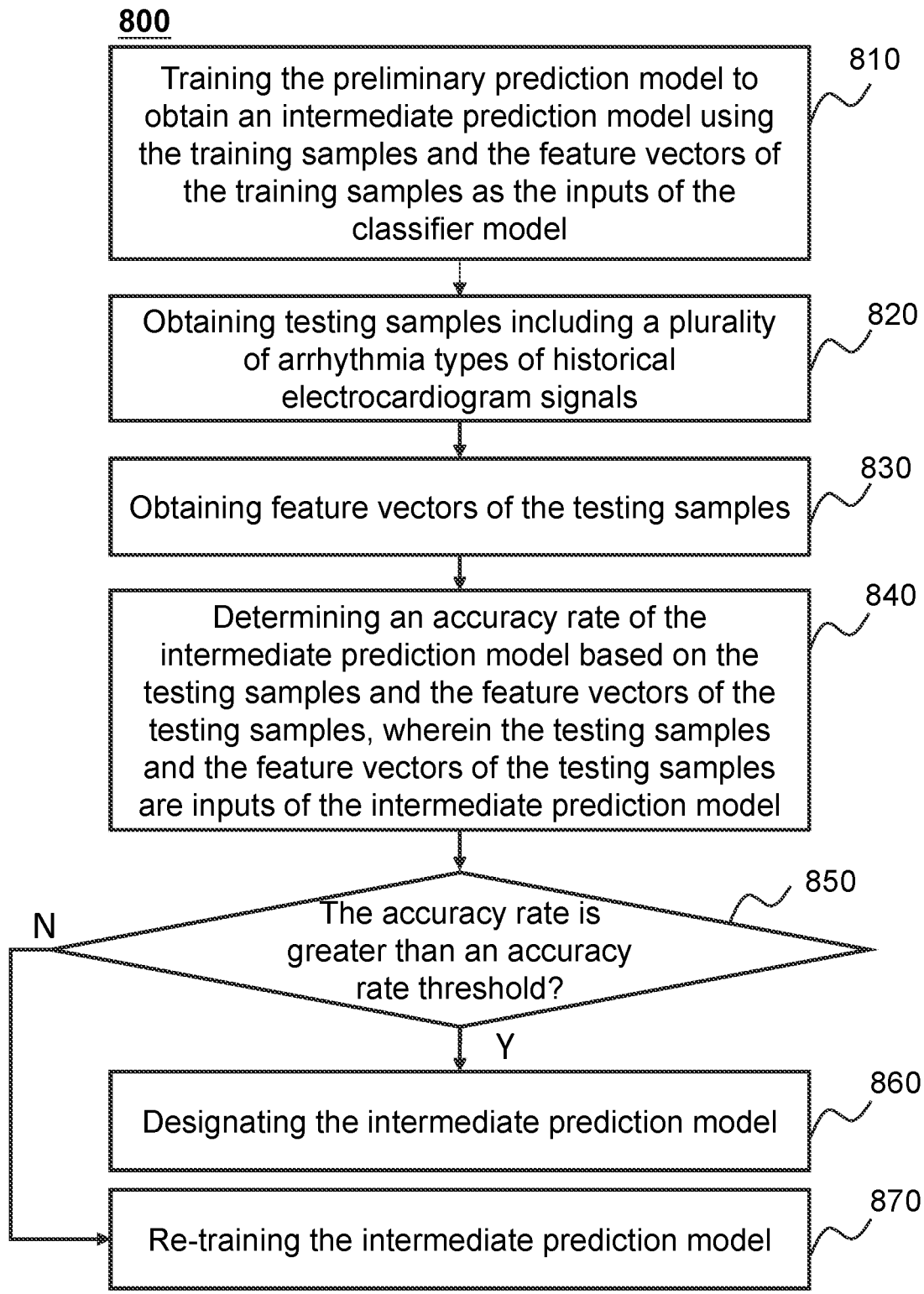
FIG. 8 is a flowchart illustrating an exemplary process and/or method for testing a prediction model according to some embodiments of the present disclosure.

FIG. 8 is a flowchart of an exemplary process and/or method for testing a prediction model according to some embodiments of the present disclosure. In some embodiments, one or more steps in the process 800 may be implemented in the system 100 illustrated in FIG. 1. For example, one or more steps in the process 800 may be stored in the storage (e.g., the storage device 130, the ROM 230, the RAM 240) as a form of instructions, and invoked and/or executed by the server 120 (e.g., the processing engine 122 in the server 120, or the processor 220 of the processing engine 122 in the server 120).

In 810, the processor 220 (or the model training module 450) may train the preliminary prediction model to obtain an intermediate prediction model using the training samples and/or the feature vectors of the training samples as the inputs of the classifier model. In some embodiments, the training of the preliminary prediction model may be found elsewhere in the present disclosure (e.g., FIG. 7 and the description thereof). The model after training may refer to the intermediate prediction model.

In 820, the processor 220 (or the model testing module 460) may obtain testing samples including a plurality of arrhythmia types of historical ECG signals.

In some embodiments, the testing samples may include a plurality of known arrhythmia types of historical ECG signals. For example, the testing samples may include a plurality of historical ECG signals that have known arrhythmia types determined by a medical personnel. The arrhythmia types may include VT, VF, SVT, VFL, or the like, or a combination thereof.

In 830, the processor 220 (or the model testing module 460) may obtain feature vectors of the testing samples.

In some embodiments, the processor 220 may extract one feature vector from one testing sample. The feature vector may include a TCSC present feature, an L-Z complexity feature, an EMD complex number feature, a sample entropy feature, a set of wavelet transform energy feature, or the like, or a combination thereof. The method and/or process of obtaining the feature vector of the testing samples may be found elsewhere in the present disclosure (e.g., FIG. 5 and the description thereof).

In 840, the processor 220 (or the model testing module 460) may determine an accuracy rate of the intermediate prediction model based on the testing samples and/or the feature vectors of the testing samples.

In some embodiments, the testing samples and/or the feature vectors may be inputs of the intermediate prediction model. The output of the intermediate prediction model may include a plurality of predicted arrhythmia types, and each of the plurality predicted arrhythmia type corresponds to a testing sample. The processor 220 may compare the predicted arrhythmia types and the corresponding known arrhythmia types, and determine an accuracy rate of the correct prediction results. For example, the accuracy rate may equal to a ratio of a number of testing samples that the predicted arrhythmia types are the same as their known arrhythmia types to a total number of the testing samples that input into the intermediate prediction model.

In 850, the processor 220 (or the model testing module 460) may determine whether the accuracy rate of the intermediate prediction model is greater than an accuracy threshold.

In some embodiments, the accuracy rate may refer to an indicator that indicates whether the intermediate prediction model is well trained to predict a reliable arrhythmia type of a new ECG signal. The accuracy threshold may be a preset percentage value that stored in a storage (e.g., the storage device 130, the ROM 230, the RAM 240) of the system 100, or may be determined according to different application scenarios (e.g., different prediction model types). For example, an accuracy rate of a random forest model may be 85%, and an accuracy rate of a BP neural network model may be 83%.

In response to determining that the accuracy rate is greater than the accuracy threshold, the processor 220 may proceed 860. In 860, the processor 220 (or the model testing module 460) may designate the intermediate prediction model as the trained prediction model.

In some embodiments, the intermediate prediction model may be designated as the trained prediction model, and stored into a storage device (e.g., the storage device 130, the ROM 230, the RAM 240) of the system 100. In some embodiments, the intermediate prediction model may be used as the trained prediction model to determine (or predict) an arrhythmia type of a new ECG signal as illustrated in FIG. 5 in the present disclosure.

In response to determining that the accuracy rate is not greater than the accuracy threshold, the processor 220 may proceed 870. In 870, the processor 220 (or the model testing module 460) may re-train the intermediate prediction model.

In some embodiments, the processor 220 may input a plurality of training samples and/or the feature vectors thereof into a preliminary prediction model to obtain a new intermediate prediction model as illustrated in FIG. 7 in the present disclosure. In some embodiments, the plurality of training samples that are used to obtain the new intermediate prediction model may be different from the plurality of training samples that are used to obtain the original intermediate prediction model may be different from each other. For example, the plurality of training samples that are used to obtain an intermediate prediction model (either the new intermediate prediction model or the original intermediate prediction model) may be obtained randomly or by the bootstrap sample method. In some embodiments, the processor 220 may also test the new intermediate prediction model as illustrated in FIG. 8 in the present disclosure until the accuracy rate of the new intermediate prediction model is greater than the accuracy rate threshold, the processor 220 may designate the new intermediate prediction model as the trained prediction model.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional steps (e.g., a storing step, a preprocessing step) may be added elsewhere in the exemplary process/method 800.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment," "one embodiment," or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code) or combining software and hardware implementation that may all generally be referred to herein as a "block," "module," "engine," "unit," "component," or "system." Furthermore, aspects of the present disclosure may take the form of a computer program product embodied in one or more computer-readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 1703, Perl, COBOL 1702, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a software as a service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

We claim:

1. A system for determining an arrhythmia type, the system comprising:
   at least one storage device including a set of instructions for determining an arrhythmia type; and
   at least one processor in communication with the storage device, wherein when executing the set of instructions, the at least one processor is directed to:
   obtain an electrocardiogram signal;
   obtain a feature vector of the electrocardiogram signal;
   obtain a trained prediction model; and
   determine an arrhythmia type of the electrocardiogram signal based on the trained prediction model and the feature vector, wherein the feature vector includes at least two of a threshold crossing sample (TCSC) percent feature, an L-Z complexity feature, an empirical mode decomposition (EMD) complex number feature, a sample entropy feature, or a set of wavelet transform energy features.

2. The system of claim 1, wherein the trained prediction model is obtained by:
obtaining training samples including a plurality of arrhythmia types of historical electrocardiogram signals;
obtaining feature vectors of the training samples;
obtaining a preliminary prediction model, the preliminary prediction model including a classifier model; and
training the preliminary prediction model to obtain the trained prediction model using the training samples and the feature vectors of the training samples as inputs of the classifier model.

3. The system of claim 2, wherein the classifier model includes at least one of: a random forest model, a BP neural network model, a support vector machine (SVM) model, or a wavelet neural network model.

4. The system of claim 2, wherein the training the preliminary prediction model to obtain the trained prediction model comprises:
training the preliminary prediction model to obtain an intermediate prediction model using the training samples and the feature vectors of the training samples as the inputs of the classifier model;
obtaining testing samples including a plurality of arrhythmia types of historical electrocardiogram signals;
obtaining feature vectors of the testing samples;
determining an accuracy rate of the intermediate prediction model based on the testing samples and the feature vectors of the testing samples, wherein the testing samples and the feature vectors of the testing samples are inputs of the intermediate prediction model;
determining whether the accuracy rate is greater than an accuracy rate threshold; and
designating the intermediate prediction model based on a result of the determination that the accuracy rate is greater than the accuracy rate threshold.

5. The system of claim 4, wherein the training the preliminary prediction model to obtain the trained prediction model further comprises:
re-training the intermediate prediction model based on a result of the determination that the accuracy rate is not greater than the accuracy rate threshold.

6. The system of claim 1, wherein the arrhythmia type includes at least one of: a Ventricular Fibrillation (VF), a Ventricular Tachycardia (VT), a Ventricular Flutter (VFL), or a Supraventricular tachycardia (SVT).

7. A method for determining an arrhythmia type, implemented on a computing device having at least one processor and at least one storage device, the method comprising:
obtaining an electrocardiogram signal;
obtaining a feature vector of the electrocardiogram signal;
obtaining a trained prediction model; and
determining an arrhythmia type of the electrocardiogram signal based on the trained prediction model and the feature vector, wherein the feature vector includes at least two of a threshold crossing sample (TCSC) percent feature, an L-Z complexity feature, an empirical mode decomposition (EMD) complex number feature, a sample entropy feature, or a set of wavelet transform energy features.

8. The method of claim 7, wherein the trained prediction model is obtained by:
obtaining training samples including a plurality of arrhythmia types of historical electrocardiogram signals;
obtaining feature vectors of the training samples;
obtaining a preliminary prediction model, the preliminary prediction model including a classifier model; and
training the preliminary prediction model to obtain the trained prediction model using the training samples and the feature vectors of the training samples as inputs of the classifier model.

9. The method of claim 8, wherein the classifier model includes at least one of: a random forest model, a BP neural network model, a support vector machine (SVM) model, or a wavelet neural network model.

10. The method of claim 8, wherein training the preliminary prediction model to obtain the trained prediction model comprises:
training the preliminary prediction model to obtain an intermediate prediction model using the training samples and the feature vectors of the training samples as the inputs of the classifier model;
obtaining testing samples including a plurality of arrhythmia types of historical electrocardiogram signals;
obtaining feature vectors of the testing samples;
determining an accuracy rate of the intermediate prediction model based on the testing samples and the feature vectors of the testing samples, wherein the testing samples and the feature vectors of the testing samples are inputs of the intermediate prediction model;
determining whether the accuracy rate is greater than an accuracy rate threshold; and
designating the intermediate prediction model based on a result of the determination that the accuracy rate is greater than the accuracy rate threshold.

11. The method of claim 10, wherein training the preliminary prediction model to obtain the trained prediction model further comprises:
re-training the intermediate prediction model based on a result of the determination that the accuracy rate is not greater than the accuracy rate threshold.

12. The method of claim 7, wherein the arrhythmia type includes at least one of: a Ventricular Fibrillation (VF), a Ventricular Tachycardia (VT), a Ventricular Flutter (VFL), or a Supraventricular tachycardia (SVT).

13. A non-transitory computer-readable medium, comprising at least one set of instructions for determining an arrhythmia type, when executed by at least one processor of a computer device, the at least one set of instructions directs the at least one processor to:
obtain an electrocardiogram signal;
obtain a feature vector of the electrocardiogram signal;
obtain a trained prediction model; and
determine an arrhythmia type of the electrocardiogram signal based on the trained prediction model and the feature vector, wherein the feature vector includes at least two of a threshold crossing sample (TCSC) percent feature, an L-Z complexity feature, an empirical mode decomposition (EMD) complex number feature, a sample entropy feature, or a set of wavelet transform energy features.

14. The non-transitory computer-readable medium of claim claim 13, wherein the trained prediction model is obtained by:

obtaining training samples including a plurality of arrhythmia types of historical electrocardiogram signals;

obtaining feature vectors of the training samples;

obtaining a preliminary prediction model, the preliminary prediction model including a classifier model; and training the preliminary prediction model to obtain the trained prediction model using the training samples and the feature vectors of the training samples as inputs of the classifier model.

15. The non-transitory computer-readable medium of claim 14, wherein the classifier model includes at least one of: a random forest model, a BP neural network model, a support vector machine (SVM) model, or a wavelet neural network model.

16. The non-transitory computer-readable medium of claim 14, wherein the training the preliminary prediction model to obtain the trained prediction model comprises:

training the preliminary prediction model to obtain an intermediate prediction model using the training samples and the feature vectors of the training samples as the inputs of the classifier model;

obtaining testing samples including a plurality of arrhythmia types of historical electrocardiogram signals;

obtaining feature vectors of the testing samples;

determining an accuracy rate of the intermediate prediction model based on the testing samples and the feature vectors of the testing samples, wherein the testing samples and the feature vectors of the testing samples are inputs of the intermediate prediction model;

determining whether the accuracy rate is greater than an accuracy rate threshold; and designating the intermediate prediction model based on a result of the determination that the accuracy rate is greater than the accuracy rate threshold.

17. The non-transitory computer-readable medium of claim 13, wherein the arrhythmia type includes at least one of: a Ventricular Fibrillation (VF), a Ventricular Tachycardia (VT), a Ventricular Flutter (VFL), or a Supraventricular tachycardia (SVT).

* * * * *